United States Patent [19]

Saunders et al.

[11] 3,951,999

[45] Apr. 20, 1976

[54] ANTI-INFLAMMATORY 1,2-BENZISOXAZOLE DERIVATIVES

[75] Inventors: John Christopher Saunders, Maidenhead; William Robert Nigel Williamson, Slough, both of England

[73] Assignee: Lilly Industries, Ltd., London, England

[22] Filed: Oct. 16, 1974

[21] Appl. No.: 515,131

[30] Foreign Application Priority Data

Oct. 23, 1973 United Kingdom............... 49259/73

[52] U.S. Cl. .................... 260/307 DA; 260/469; 260/471 R; 260/473 S; 260/517; 260/518 A; 260/519; 260/566 A; 260/566 AE; 260/566 B; 424/272

[51] Int. Cl.² ...................................... C07D 261/20

[58] Field of Search ............................. 260/307 DA

[56] References Cited

OTHER PUBLICATIONS

Meisenheimer et al.— C.A. 22, 3887–3888 (1928).
Reich et al.— C.A. 51, 7354e (1957).
Bianchi et al.— C.A. 65, 7161d (1966).

*Primary Examiner*—Raymond V. Rush
*Attorney, Agent, or Firm*—James L. Rowe; Everet F. Smith

[57] ABSTRACT

3-Phenyl substituted 1,2-benzisoxazole acetic and propionic acid derivatives with anti-inflammatory activity.

4 Claims, No Drawings

ANTI-INFLAMMATORY 1,2-BENZISOXAZOLE DERIVATIVES

This invention relates to certain new heterocyclic compounds and in particular to certain novel 1,2-benzisoxazole derivatives which have been found to possess valuable pharmacological activity and/or are useful as intermediates for preparing such active compounds and to a process by which such compounds may be prepared. The invention also includes pharmaceutical compositions containing said pharmacologically active compounds and a method of treating animals including humans comprising administering thereto an effective dose of said compounds or compositions.

According to the present invention there are provided novel 1,2-benzisoxazole derivatives of the formula:

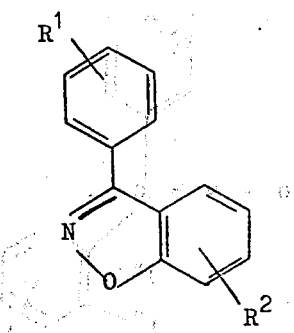

I wherein $R^1$ represents one or more substituents which are at any one or more of the available positions in the benzene ring and which are selected from one or more of the following atoms or groups: hydrogen, halogen, preferably chlorine or bromine $C_{1-4}$ alkyl, preferably methyl, $C_1-C_4$ alkoxy, preferably methoxy, nitro, and trifluoromethyl, and $R^2$ is a substituent at the 5-, 6-, or 7- position of the 1,2-benzisoxazole nucleus and is one of the following: hydrogen, $C_{1-4}$ alkyl, preferably methyl, carboxy $C_{1-4}$ alkyl, preferably carboxymethyl, cyano $C_{1-4}$ alkyl, preferably cyanomethyl or 1-cyanoethyl, $-CH(R^3)$.COOH, $-CH_2.COOR^3$, and $-CH(R^3).COOR^3$, where $R^3$ is $C_{1-4}$ alkyl; except that when $R^1$ represents a hydrogen atom $R^2$ is not hydrogen.

Compounds in which $R^2$ is halo $C_{1-4}$ alkyl are useful as intermediates.

The terms "$C_{1-4}$ alkyl" and "$C_{1-4}$ alkoxy" as used herein mean a straight or branched chain alkyl or alkoxy group containing from 1 to 4 carbon atoms, that is methyl-, ethyl-,n-propyl-, iso-propyl-,n-butyl-,s-butyl- or t-butyl-. The term "carboxymethyl" as used herein means, of course, the group $-CH_2CO_2H$.

A preferred class of compounds of formula I are those in which $R^2$ represents a carboxymethyl group or a group of formula $-CH(R^3)COOH$. In this preferred class there exists a still further preferred class, namely those in which $R^1$ represents a halogen substituent, particularly a para halo-substituent.

A presently preferred compound of the invention is α-methyl-3-p-chlorophenyl-1,2-benzisoxazol-7-yl acetic acid.

The present invention also provides a process for preparing the novel 1,2-benzisoxazole derivatives of the invention which process comprises cyclising a compound of the following formula.

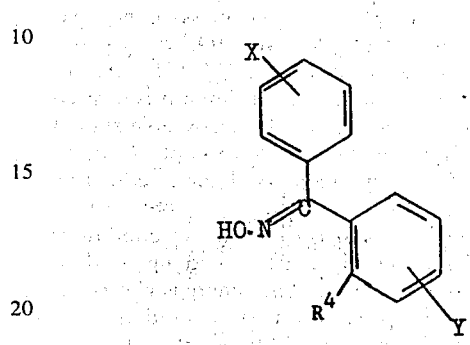

wherein $R^4$ is hydroxy or halogen (preferably chloro or bromo and especially the latter), X and Y are respectively $R^1$ and $R^2$ as hereinbefore defined or, independently, either or both of X and Y represent a group which is convertible to the desired groups $R'$ or $R^2$, respectively, and thereafter then either or both of X and Y represent a group which is convertible to the desired group $R^1$ or $R^2$, respectively, the said group X and/or Y is converted to the group $R^1$ and/or $R^2$ in conventional manner.

Alternatively, an obvious chemical equivalent of the oxime such as a hydrazone can be used in the ring-closure reaction.

Conveniently a pecursor of the oxime of formula II, or the hydrazone, is the corresponding benzophenone derivative, which may be synthesised by methods well known in the art. The benzophenone may be reacted with hydroxylamine to produce the oxime, or reacted with a suitable hydrazine to yield the hydrazone.

This reaction can be represented by the following reaction scheme:

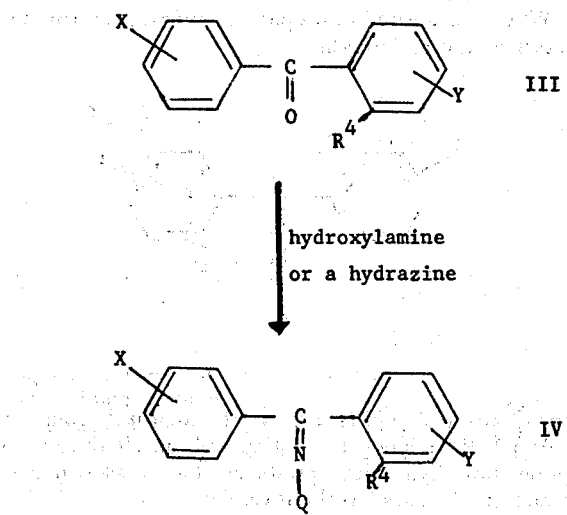

where Q is a hydroxyl or amino group. The above conversion, when X is not hydrogen, is novel and is thus provided in a further aspect of the invention. Similarly, when X is not hydrogen, the intermediates of formula IV are novel. The intermediates of formula IV where $R^4$ is hydroxyl are particularly valuable since, as well as being convertible to benzioxazoles according to the invention, they are also (by choosing appropriate reaction conditions) convertible to the class of benzoxazoles described in Belgian Pat. No. 799,790 or pending U.S. patent applicaion Ser. No. 356,251. The appropriate reaction conditions to use when it is desired that a benzoxazole rather than a benzisoxazole should be prepared are well-known see, for example, Chapter 6, of "Heterocycle Compounds", Volume 5, edited by Elderfield and published in 1957 by John Wiley. Briefly, to obtain the benzoxazole, acidic conditions (e.g. using polyphosphoric acid) should be used to effect a Beckmann rearrangement, whereas if it is desired to obtain a benzisoxazole basic conditions (e.g. using $Na_2CO_3$ in triglyme) should be employed.

In the case where $R^4$ is hydroxy, acylation of the appropriate oxime stereoisomer followed by heating, if necessary, effects the cyclisation, although it is possible to ring-close the oxime direct.

The hydrogen atom from the $R^4$ hydroxyl group can be replaced by a group IA metal, such as sodium, a group IA metal or ammonium ion.

In the case where the compound of formula VI in which $R^4$ is hydroxy is cyclised to the benzisoxazole, the configuration of the intermediate:-

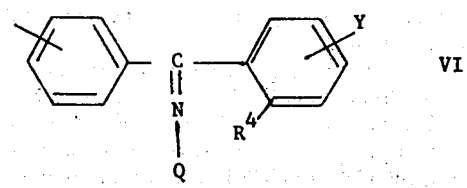

VI should be such that the Q group is anti- to the phenolic hydroxyl group. When $R^4$ is halo, the Q group should be syn thereto.

When it is desired to prepare a benzoxazole from the intermediate of formula :

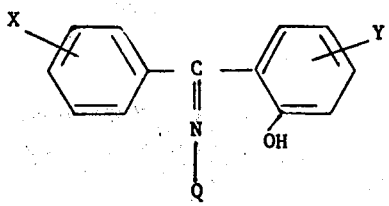

the Q group should be anti- to the hydroxyl group.

When $R^4$ is halogen, heating with an alkali such as potassium hydroxide produces the benzisoxazole, which in all cases has the formula:

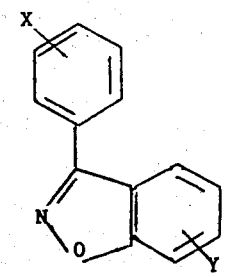

VII wherein X and Y are as previously defined.

Thus, in general terms, the present invention provides a process for preparing a compound of formula I which comprises the ring-closure under basic conditions of a compound of formula:

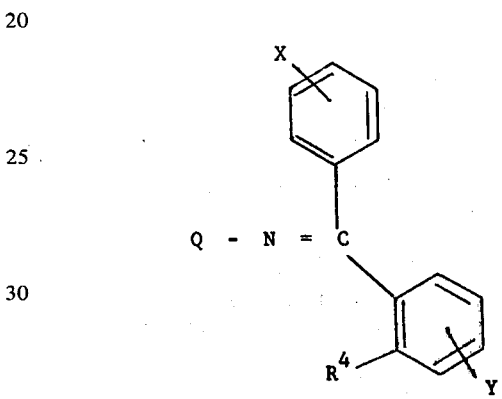

where X and Y are as previously defined, Q is a hydroxyl, amino, acyloxy (preferably a group of formula

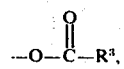

where $R^3$ is $C_{1-4}$ alkyl) or sulphonyloxy radical, and $R^4$ is halogen or a group of formula —OM where M is hydrogen, ammonium or a group IA or IIA metal, followed, if necessary, by the conversion of X and/or Y to the desired $R^1$ and/or $R^2$ groups by conventional means.

For example, when Y represents alkyl, the alkyl group may be halogenated using conventional halogenating agents such as chlorine, sulphuryl chloride, bromine, or N-bromosuccinnimide, preferably in the presence of a suitable solvent such as carbon tetrachloride, and thereafter a cyano group substituted for the halogen atom. Hydrolysis of the nitrile produces the corresponding carboxylic acid which may if desired be esterified. Alternatively, the halogen atom can be replaced by a carboxylic acid group via an organometallic compound such as a Grignard reagent. This procedure is fully described in Standard reference books, for example for the Grignard reaction, see page 11 72 of the Merck Index, VIIIth Edition, published 1968. Acids or esters Formula I may be alkylated at the α-carbon atom using an alkyl halide such as methyl or ethyl iodide. An ester of formula I may also be converted to the hydroxamic acid derivative by reaction with hydroxylamine.

An acid of formula I may be salified by treatment with an appropriate base such as ammonium, alkylammonium, aralkylammonium, alumium, alkali metal or alkaline earth metal hydroxide and of course a salt of formula I may readily be converted to the free acid by treatment with an acid such as hydrochloric or sulphuric acid. The salts, e.g. the sodium salt, are pharmaceutically active. An acid of formula I or a salt thereof may be converted to an ester by treatment with an appropriate alcohol or by treatment with a halide of the appropriate ester moiety or a salt of that halide if the ester moiety contains a basic nitrogen atom. An ester of formula I may, of course, be hydrolysed to the corresponding acid of formula I by treatment with a suitable hydrolytic agent such as an inorganic base or acid. An acid of formula I or an ester thereof may also be converted to an amide of formula I by reaction with ammonia or an appropriate primary or secondary amine.

It will be understood that the above described specific cyclisation procedure is not the only method of synthesising the novel compounds of this invention; any obvious chemical equivalent cyclisation reaction may be employed, that is any reaction, or sequence of reactions, which is capable of bringing a nitrogen atom and/or an oxygen atom into the desired relationship with the benzophenone derivative so as to produce a compound of formula VII.

As mentioned above, the acids of formula I, i.e. those compounds in which $R^2$ is carboxymethyl or $-CH(R^3)COOH$ are preferred compounds of the invention. These acids can be prepared by hydrolysis of the corresponding nitriles of formula VII where Y is cyano $C_{1-4}$ alkyl. Clearly, when it is desired to prepare the acid in which $R^2$ is carboxymethyl, cyanomethyl is the group which needs to be hydrolysed. Similarly, when it is desired to produce an acid group of formula $-CH(R^3)COOH$ it is necessary to hydrolyse a group of formula $-CH(R^3)CN$.

Alternatively, the above class of acids can be prepared from derivatives of formula I where $R^2$ is a $C_{1-4}$ haloalkyl group using the Grignard reaction. After reaction with magnesium and treatment with carbon dioxide a compound of formula I is formed in which $R^2$ represents the group

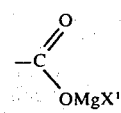

where $X^1$ is a halogen atom. This group can then be converted to a carboxylic acid group simply by hydrolysis.

Thus, according to yet a further feature of the invention there is provided a method of preparing an acid of formula:

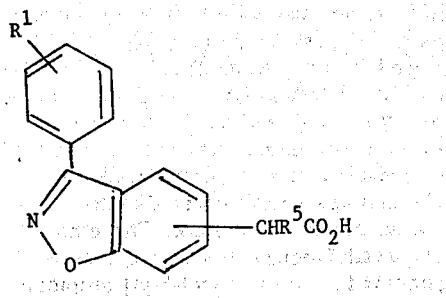

wherein $R^1$ is as defined previously and $R^5$ represents hydrogen or $C_{1-4}$ alkyl, which comprises hydrolysing a compound of formula:

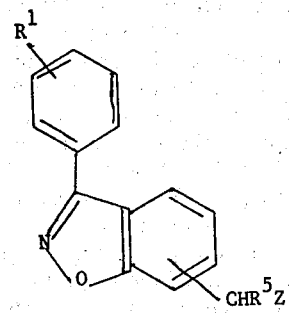

where Z represents a nitrile, ester, carboxylate or hydroxamic acid group, or a group of formula:

where $X^1$ is a halogen atom.

The novel compounds of the present invention in which $R^2$ is a carboxy or esterified carboxy moiety have been found to possess anti-inflammatory activity and in some cases other pharmacological activity, whilst the other novel compounds of formula I are useful as intermediates in the synthesis of the aforementioned pharmacologically active compounds. The pharmacological activity has been demonstrated in tests carried out in animals, usually at doses of from 0.1 to 500 mg./Kg. In the treatment of humans, the dose administered may be, for example, between 0.1 and 25 mg./kg. but, of course, doses outside this range may be used at the discretion of the physician treating the patient. The pharmacologically active compounds of formula I may be administered by the enteral or parenteral routes and for this purpose they will normally be formulated into pharmaceutical compositions comprising the active ingredient in association with at least one pharmaceutically acceptable carrier therefor. Such compositions form a part of this invention and will normally consist of the active ingredient mixed with a carrier, or diluted by a carrier, or enclosed or encapsulated by a carrier in the form of a capsule, sachet, cachet or other container. The carrier may be a solid, semi-solid or liquid material which serves as a vehicle, excipient, coating agent, or medium for the active ingredient. Some examples of the carriers which may be used are lactose, dextrose, sucrose, sorbitol, mannitol, starch, gum acacia, calcium phosphate, liquid paraffin, cocoa butter, oil of theobroma, alginates, tragacanth, gelatin, methyl cellulose, polyoxyethylene sorbitan monolaurate, methyl — or propyl — hydroxybenzoate, ethyl cellulose acetate phthalate, low viscosity acetyl cellulose acetate, paraffin wax, mineral wax, vegetable wax, vegetable gum, silicone rubbers such as liquid polydimethylsiloxane rubber, plasticised or unplasticised polyvinyl chloride, plasticised polyethylene terephthalate, modified collagen, cross-linked hydrophilic polyether gel, cross-linked polyvinyl alcohol or cross-linked partially hydrolysed polyvinyl acetate.

Advantageously the compositions of the invention are formulated in a dosage unit form containing from 1 to 1000 mg. (preferably 25 to 500 mg.) of the active ingredient. Examples of suitable dosage unit forms are tablets, hard or soft gelatin capsules, microcapsules and suppositories as well as drug dispensing systems comprising the active ingredient contained in a flexible, imperforate polymeric material through which the drug may be released slowly by diffusion. More generally, the term "dosage unit form" as used herein means a physically discrete unit containing the active ingredient, generally in admixture with and/or enclosed by a pharmaceutical carrier, the quantity of active ingredient being such that one or more units are normally required for a single therapeutic administration.

In addition to the active ingredient of formula I, the compositions of the present invention may also contain one or more pharmacologically active ingredients, for example, acetylsalicyclic acid and salts thereof, caffeine, codeine phosphate, phenylbutazone, paracetamol, dextropropoxyphene and indomethacin.

The compositions of the present invention will of course be adapted to the particular route of administration. Thus, for oral administration, tablets, pills, capsules, solutions or suspensions may be used; for parenteral administration, sterile injection solutions or suspensions may be used; for rectal administration, suppositories may be used; and for topical administration, creams, lotions or ointments may be used. Any of the foregoing compositions may, of course, be formulated in delayed or sustained release form in a manner well known in the art.

The following examples will further illustrate the invention. No examples of the formation of acids via the Grignard route are given. However, those skilled in the art will appreciate that the haloalkyl intermediates described hereinafter can be converted to the corresponding acids by this method, if so desired.

Example 1

5-Methyl-3-(4-chlorophenyl)-1,2-benzisoxazole

2-Hydroxy-5-methyl-4¹-chlorobenzophenone (13.5 g, 0.55 moles) was stirred with a solution of potassium hydroxide (44 g.) in water (150 ml.) and then hydroxylamine hydrochloride (17.4 g, 0.25 mole) was added with ice cooling. After stirring overnight at room temperature 100 ml. of water was added and the mixture was acidified with 5N-hydrochloric acid to give an off-white precipitate which was filtered, washed and dried (14.7 g.). Recrystallisation of the product from benzene gave the oxime (7 g.) m.p. 163°C. (This is the stereo isomer in which the oxime —OH group and the p-chlorophenyl group are in the syn positions relative to each other, and is therefore the correct isomer for the next stage).

The above oxime (5 g, 0.019 mole) was heated on the steam bath with acetic anhydride (10 ml.) until it all dissolved and then for 5 minutes longer. The solution was evaporated in vacuo to a clear oil which crystallised to give a white solid on cooling. This was heated under nitrogen at 290°–300°C. for 5 minutes and acetic acid distilled over. The product was distilled in vacuo to give 5-methyl-3-(4-chlorophenyl)-1,2-benzisoxazole (2.4 g.), b.p. 154°–158°C/ 0.2 mm. After purification by preparative t.l.c. an off-white solid; m.p. 95°C. was obtained. This compound was also prepared by boiling 2-bromo-5-methyl-4¹-chlorobenzophenone oxime with alcoholic potassium hydroxide solution.

EXAMPLE 2

5-Bromomethyl-3-(4-chlorophenyl)-1,2-benzisoxazole

N-Bromosuccinimide (26 g.) was added to a cold solution of 5-methyl-3-(4-chlorophenyl)-1,2-benzisoxazole (35 g.) in carbon tetrachloride (250 ml.). Benzoyl peroxide (500 mg.) was added and the mixture was heated under reflux for 3 hours in the presence of U.V. light. The solid residue was filtered off, and the filtrate was evaporated to give 5-bromomethyl-3-(4-chlorophenyl)-1,2-benzisoxazole (m.p. 142°C.).

EXAMPLE 3

3-(4-Chlorophenyl)-1,2-benzisoxazol-5-ylacetonitrile

A mixture of 5-bromomethyl-3-(4-chlorophenyl)-1,2-benzisoxazole (45 g.) and sodium cyanide (7.4 g.) in dry dimethylformamide (800 ml.) was heated on a steam bath for 3 hours. The mixture was filtered and the filtrate was evaporated to dryness, to give 3-(4-chlorophenyl)-1,2-benzisoxazol-5-ylacetonitrile (m.p. 118°C.).

EXAMPLE 4

3-(4-Chlorophenyl)-1,2-benzisoxazol-5-yl acetic acid

A solution of the above nitrile (11 g.) in concentrated hydrochloric acid (100 ml.) was heated on a steam bath for 1 hour. The solution was then allowed to cool, evaporated to dryness and the product dissolved in chloroform. The chloroform solution was repeatedly extracted with sodium bicarbonate solution. The combined extracts were acidified to give 3-(4-chlorophenyl)-1,2-benzisoxazol-5-yl acetic acid, (m.p. 189°C.).

EXAMPLE 5

Ethyl 3-(4-chlorophenyl)-1,2-benzisoxazol-5-yl acetate

A solutiion of 3-(4-chlorophenyl)-1,2-benzisoxazol-5-yl acetic acid (20 g.) in ethanol (200 ml.) was heated under reflux for 6 hours, during which time dry hydrogen chloride gas was passed through the solution. The solution was evaporated to dryness, the residue treated with sodium bicarbonate solution and the product extracted with ether. The extract, after drying (Na₂SO₄) and evaporation, gave ethyl 3-(4-chlorophenyl)-1,2-benzisoxazol-5-yl acetate.

EXAMPLE 6

Ethyl 2-[3-(4-chlorophenyl)-1,2-benzisoxazol-5-yl]propionate

A solution of ethyl 3-(4-chlorophenyl)-1,2-benzisoxazol-5-yl acetate (39 g.) in ether (200 ml.) was added to a stirred solution of sodamide (from the 3.2 g sodium) in liquid ammonia (500 ml.). This mixture was stirred for 15 minutes, then a solution of methyl iodide (8.5 ml.) in ether (10 ml.) was added rapidly. When the reaction mixture became colourless the reaction was stopped by the addition of excess ammonium chloride. The mixture was evaporated to dryness and the residue was extracted with ether. The ethereal solution was evaporated to dryness to yield ethyl 2-[3-(4-chlorophenyl)-1,2-benzisoxazol-5-yl] propionate.

EXAMPLE 7

2-[3-(4-Chlorophenyl)-1,2-benzisoxazol-5-yl] propionic acid

A solution of ethyl 2-[3-(4-chlorophenyl)-1,2-benzisoxazol-5-yl] propionate (15 g.) in concentrated hydrochloric acid (150 ml.) was heated on a steam bath for 6 hours. The solution was cooled and the crystals which formed were filtered off and recrystallized to yield 2-[3-(4-chlorophenyl)-1,2-benzisoxazol-5-yl]propionic acid,(m.p. 137°–9°C.) The following compounds were prepared using methods analogous to those described above:

6-Methyl-3-(4-chlorophenyl)-1,2-benzisoxazole.
7-Methyl-3-(2,4-dichlorophenyl)-1,2-benzisoxazole.
5-Methyl-3-(4-bromophenyl)-1,2-benzisoxazole.
5-Methyl-3-(4-methylphenyl)-1,2-benzisoxazole.
5-Methyl-3-(4-methoxyphenyl)-1,2-benzisoxazole.
5-Methyl-3-(4-nitrophenyl)-1,2-benzisoxazole.
5-Methyl-3-(4-trifluoromethylphenyl)-1,2-benzisoxazole.
6-Methyl-3-(4-bromophenyl)-1,2-benzisoxazole.
6-Methyl-3-(4-methylphenyl)-1,2-benzixazole.
6-Methyl-3-(4-methoxyphenyl)-1,2-benzisoxazole.
6-Methyl-3-(4-nitrophenyl)-1,2-benzioxazole.
6-Methyl-3-(4-trifluoromethyl)-1,2-benzisoxazole.

Also the following acetic and propionic acids, and their esters and corresponding nitriles:

3-Phenyl-1,2-benzisoxazol-5-ylacetic acid.
3-(4-Bromophenyl)-1,2-benzisoxazol-5-ylacetic acid.
3-(4-Methylphenyl)-1,2-benzisoxazol-5-ylacetic acid.
3-(4-Methoxyphenyl)-1,2-benzisoxazol-5-ylacetic acid.
3-(4-Nitrophenyl)1,2-benzisoxazol-5-ylacetic acid.
3-(4-Trifluoromethylphenyl)-1,2-benzisoxazol-5-ylacetic acid.
2-[3-(4-Bromophenyl)-1,2-benzioxazol-5-yl]propionic acid.
2-[3-(4-Methylphenyl)-1,2-benzisoxazol-5-yl]propionic acid.
2-[3-(4-methoxyphenyl)-1,2-benzisoxazol-5-yl]propionic acid.
2-[3-(4-Nitrophenyl)-1,2-benzisoxazol-5-propionic acid.
2-[3-(4-Trifluoromethylphenyl)-1,2-benzisoxazol-5-yl]-propionic acid.
2-[3-phenyl-1,2-benzioxazol-5-]propionic acid.
3-(4-chlorophenyl)-1,2-benzisoxazol-6-yl acetic acid
2-[3-(4-chlorophenyl)-1,2-benzisoxazol-6-yl]propionic acid
2-[3-phenyl-1,2-benzisoxazol-6-yl]propionic acid
2-[3-(4-chlorophenyl)-1,2-benzisoxazol-7-yl]propionic acid
3-(2,4-dichlorophenyl)-1,2-benzisoxazol 7-yl acetic acid
3-(2,4-dichlorophenyl)-1,2-benzisoxazol-7-yl propionic acid.

Confirmation of the correct structures of the above-named compounds was obtained by t.l.c. evidence.

EXAMPLE 8

5-Bromomethyl-3-(4-chlorophenyl)-1,2-benzisoxazole 3-(4-Chlorophenyl)-5-methyl-1,2-benzisoxazole (12.2g.) and N-bromosuccinimide (9.6g.) were mixed in carbon tetrachloride (200ml.) and heated under reflux in the presence of UV light. (Hanovia medium pressure lamp 125 watts, emitting at 254,265,297,313,366 mµ). On cooling, the mixture was filtered and the filtrate evaporated to dryness. The resulting solid was recrystallized from 33% toluene/6-0-80 petrol ether (150 ml.) to give the title compound as a white crystalline solid (10.0g) m.p. 142°C Microanalysis: $C_{14}H_9BrClNO$ requires 52.1%C, 2.8%H, 4.3%N, 11.0%Cl, 24.8%Br. Found 51.9%C, 3.0%H, 4.6%N, 10.7%Cl, 24.7%Br.

EXAMPLE 9

3-(4-Chlorophenyl)-1,2-benzisoxazol-5-ylacetonitrile

5-Bromomethyl-3-(4-chlorophenyl)-1,2-benzisoxazole(6.5g.), sodium cyanide (1.1g) and dry sodium iodide (0.3g) were stirred together in dry dimethylformamide (50ml) for 20 hours at ambient temperature. The mixture was poured into water (500ml.), stirred for one hour and the brown solid filtered off, washed and dried (5.1g). This was recrystallised, with charcoaling, from 50% toluene/60–80 petrol ether (100ml.) To give the title compound as an off-white solid (3.4g) m.p. 118°C.

Microanalysis : $C_{15}H_9ClN_2O$ requires 67.0%C, 3.4%H, 10.4%N, 13.2%Cl. Found 67.2%C, 3.6%H, 10.2%N, 13.5%Cl.

EXAMPLE 10

3-(4-Chlorophenyl)-1,2-benzisoxazol-5-ylacetic acid 3-(4-Chlorophenyl-1,2-benzisoxazol-5-ylacetonitrile (4.7g) was mixed with concentrated hydrochloric acid (40ml.) and glacial acetic acid (20ml.) and heated at 80°C. for three hours. The mixture was poured into water (300ml.) and the residue filtered off and washed with water. This solid was stirred with 5% aqueous sodium carbonate solution (200ml) and the solution was then filtered. The filtrate was acidified with 2N-hydrochloric acid giving a white precipitate which was filtered, washed and dried to give the title compound (4.2g) m.p. 189°C.

Microanalysis : $C_{15}H_{10}ClNO_3$ requires 62.6%C, 3.5%H, 4.9%N, 12.3%Cl. Found 62.5%C, 3.7%H, 5.0%N, 12.6%Cl.

EXAMPLE 11

4'-Chloro-5-ethyl-2-hydroxybenzophenone

Aluminum chloride (267g) was added in portions over 30 minutes to a stirred solution of 4-ethylphenol (122.1g.) and 4-chloro-benzoyl chloride (140ml.) in dry 1,1,2,2-tetrachloroethane (800ml.). The mixture was heated at 105°C. for 22 hours with stirring, and on cooling a mixture of ice (600g) and concentrated hydrochloric acid was added slowly, A vigorous reaction occurred and some material was lost. The remaining material was separated and the aqueous fraction extracted twice with chloroform (200ml.), and the combined organic layers evaporated to a dark oil which was distilled in vacuo giving two main fractions: B (17.4g) 150°–160°C at 0.3mmHg; C (110.8g) 160°–168°C at 0.3mmHg. Both remained liquid on cooling.

Microanalysis : $C_{15}H_{13}ClO_2$ requires 69.1%C, 5.0%H, 13.6%Cl. Found 69.0%C, 5.0%H, 13.9%Cl.

EXAMPLE 12

4'-Chloro-5-ethyl-2-hydroxybenzophenone-oxime

4'-Chloro-5-ethyl-2-hydroxybenzophenone (65.2g) and potassium hydroxide (170g) in water (700ml) and ethanol (150ml.) were treated with hydroxylamine hydrochloride (70.0g), with cooling, and the resulting mixture was stirred for 18 hours at ambient temperature. Dissolution occurred during this time. The solution was acidified with 5N-hydrochloric acid and then extracted with ether (3×200ml.). The combined ether solutions were washed with 10% aqueous sodium carbonate solution (2×200ml) and evaporated to dryness to give an off-white solid. This solid was recrystallised from 40% benzene/60–80 petrol ether to give a white crystalline solid (29.9g), second crop (14.5g.) m.p.117°C.

Microanalysis : $C_{15}H_{14}ClNO$ requires 65.3%C, 5.1%H, 5.1%N, 12.9%Cl. Found 65.3%C, 4.9%H, 5.1%N, 12.9%Cl. (Stereoisomer as in Example 1).

EXAMPLE 13

3-(4-Chlorophenyl)5-ethyl-1,2-benzisoxazole

4'-Chloro-5-ethyl-2-hydroxybenzophenone-oxime (22.0g) was dissolved in hot acetic anhydride (45ml) and immediately cooled, causing the oxime mono-acetate to crystallise. This was filtered and dried (19.7g) m.p. 105°C. The oxime mono-acetate (19.0g) and sodium carbonate (13.3g) were heated together in triglyme, under reflux, for 30 minutes. On cooling, the mixture was poured into water (1.0l.) this was extracted with ether (3×250ml). The combined ether extracts were washed with water (3×250ml) and evaporated to dryness to give a yellow oil which crystallised at room temperature (16.4G). A sample (3.0g) this solid was recrystallised from methanol/water to give a white solid (1.5g) m.p. 42°–45°C Microanalysis : $C_{15}H_{12}ClNO$ requires 69.9%C, 4.7%H, 5.4%N, 13.8%Cl. Found 69.6%C, 4.8%H, 5.4%N, 13.8%Cl.

EXAMPLE 14

5-(1-Bromoethyl)-3-(4-chlorophenyl)-1,2-benzisoxazole 3-(4-Chlorophenyl)-5-ethyl-1,2-benzisoxazole (12.3g) was brominated similarly to Example 8, to give the title compound (11.3g), m.p. 111°–6°C. Microanalysis : $C_{15}H_{11}BrClNO$ requires 53.5%C, 3.3%H, 4.2%N, 10.5%Cl, 23.7%Br. Found 53.6%C, 3.5%H, 4.0%N, 10.3%Cl, 24.0%Br.

EXAMPLE 15

2-[3-(4-Chlorophenyl)-1,2-benzisoxazol-5-yl]-propionitrile 5-(1-Bromoethyl)-3-(4-chlorophenyl)-1,2-benzisoxazole (9.0g) was treated with sodium cyanide in a similar manner to Example 9 to give the title compound as a viscous yellow oil (6.4g).

EXAMPLE 16

2-[3-(4-Chlorophenyl)-1,2-benzisoxazol-5-yl]-propionic acid

2-[3-(4-Chlorophenyl)-1,2-benzisoxazol-5-yl]-propionitrile (6.4g) was hydrolysed similarly to Example 10 to give an off-white solid (5.1g.). This was recrystallised from toluene with charcoaling to give the title compound (3.9g) m.p. 137°–9°C.

EXAMPLE 17

4'-Chloro-4-ethyl-2-hydroxybenzophenone

3-Ethylphenol (122.1g) was reacted with 4-chlorobenzoyl chloride (140ml) similarly to Example 11, giving two main fractions on distillation A (141.8g) 155°–160°c at 0.09 mmHg; B(15.3g.) 150°–170°C at 0.09 mmHg. Both fractions contained about 80% of the title compound, plus 20% of the isomer. 4'-chloro-2-ethyl-4-hydroxybenzophenone, and the mixture used in Example 18.

EXAMPLE 18

4'-Chloro-4-ethyl-2-hydroxybenzophenone-oxime

4'-Chloro-4-ethyl-2-hydroxybenzophenone (130.4g) was treated with hydroxylamine hydrochloride (140g) similarly to Example 12, to give the title compound, one isomer only (81.2g), m.p. 159°–161°C, Microanalysis : $C_{15}H_{14}ClNO$ requires 65.3%C, 5.1%H, 5.1%N, 12.9%Cl. Found 65.6%C, 5.1%H, 5.4%N, 12.8%Cl. Stereoisomer as an Example 1.

EXAMPLE 19

3-(4-Chlorophenyl)-6-ethyl-1,2-benzisoxazole

4'-Chloro-4-ethyl-2-hydroxybenzophenone (44.0g) was treated with acetic anhydride similarly to Example 13, to give the oxime-monoacetate (42.7g). This was immediately converted to the title compound as in Example 13 (34.7g.). 8.9 g of this was recrystallised from methanol/water to give a white crystalline solid (6.5g), m.p. 78°–9°C. Microanalysis : $C_{15}H_{12}ClNO$ requires 69.9%C, 4.7%H, 5.4%N, 13.8%Cl. Found 69.6%C, 4.7%H, 5.2%N, 13.8%Cl.

EXAMPLE 20

6-(1-Bromoethyl)-3-(4-chlorophenyl)-1,2-benzisoxazole 3-(4-Chlorophenyl)-6-ethyl-1,2-benzisoxazole (25.8g) was brominated similarly to Example 8 to give the title compound (22.2g), which was used without further purification.

EXAMPLE 21

2-[3-(4-Chlorophenyl)-1,2-benzisoxazol-6-yl]-propionitrile 6-(1-Bromoethyl)-3-(4-chlorophenyl)-1,2-benzisoxazole (16.8g) was treated with sodium cyanide in a similar manner to Example 9 to give the title compound as an off-white solid (10.0g), which was used without further purification.

EXAMPLE 22

2-[3-(4-Chlorophenyl)-1,2-benzisoxazol-6-yl]-propionic acid

2-[3-(4-Chlorophenyl)-1,2-benzisoxazol-6-yl]-propionitrile (10.0g) was hydrolysed similarly to Example 10 to give the title compound as a white solid (1.8g), m.p. 176°–9°C.

Microanalysis : $C_{16}H_{12}ClNO_3$ requires 63.7%C, 4.0%H, 4.6%N, 11.8%Cl. Found 63.4%C, 4.1%H, 4.6%N, 11.5%Cl.

EXAMPLE 23

4-Ethyl-4'-fluoro-2-hydroxybenzophenone

3-Ethylphenol (24.4g) and 4-fluorobenzoyl chloride (34.9g) were reacted together as in Example 11 giving three main fractions: B (11.4g) 126°–129°C at 0.07 mmHg; C (7.9g), 129°–132°C at 0.06 mmHg; D (5.9g), 132°–150°C at 0.06 mmHg, all containing ~80% of the required isomer. B (4.0g) was separated by preparative thin layer chromatography to give the title compound (2.6g), m.p. 44°–48°C.

EXAMPLE 24

4-Ethyl-4'-fluoro-2-hydroxybenzophenone-oxime

4-Ethyl-4'-fluoro-2-hydroxybenzophenone (21.0g, 80% pure) was treated with hydroxylamine hydrochloride (24.0g) similarly to Example 12, to give, after recrystallisation from benzene, the title compound as a white crystalline solid (10.7g), m.p. 130°–2°C.

Microanalysis : $C_{15}H_{14}FNO_2$ requires 69.5%C, 5.4%H, 5.4%N, 7.3%F. Found 69.2%C, 5.5%H, 5.2%N, 7.2%F.

EXAMPLE 25

6-Ethyl-3-(4-fluorophenyl)-1,2-benzisoxazole

4-Ethyl-4'-fluoro-2-hydroxybenzophenone-oxime (9.6g) was treated with acetic acid anhyride similarly to Example 13 to give the oxime mono-acetate (7.5g). This was immediately converted to the title compound as in Example 19 (5.7g).

EXAMPLE 26

6-(1-Bromoethyl)-3-(4-fluorophenyl)-1,2-benzisoxazole

6-Ethyl-3-(4-fluorophenyl)-1,2-benzisoxazole (3.5g) was brominated similar to Example 8 to the title compound (4.1g), which was used without further purification.

EXAMPLE 27

2-[3-(4-Fluorophenyl)-1,2-benzisoxazol-6-yl]-propionitrile 6-(1-Bromoethyl)-3-(4-fluorophenyl)-1,2-benzisoxazole (4.1g) was treated with sodium cyanide in a similar manner to Example 9 to give the title compound as a brown solid (3.8g), which was used without further purification.

EXAMPLE 28

2-[3-(4-Fluorophenyl)-1,2-benzisoxazol-6-yl]-propionic acid

2-[3-(4-Fluorophenyl)-1,2-benzisoxazol-6-yl]-propionitrile (3.8g) was hydrolysed similarly to Example 10 to give the title compound as an off-white solid (0.45g) m.p. 151°–4°C.

EXAMPLE 29

3-(4-chlorophenyl)-5-methyl-1,2-benzisoxazole

4'-Chloro-2-hydroxy-4-methylbenzophenone-oxime (0.2g) and anhydrous sodium carbonate (0.2g) were heated together under reflux in triglyome (5ml) for 30 minutes. On cooling, the mixture was poured into water (50ml.) and filtered. On standing a solid separated from the filtrate and was filtered, washed, dried and examined by NMR. The NMR spectrum was consistent with the preparation of the title compound (~30%). T.L.C. also confirmed the presence of the benzisoxazole.

EXAMPLE 30

2-Hydroxy-3-methyl-4'-chlorobenzophenone

Chlorobenzene (78.79g, 71.6ml; 0.7mole), $AlCl_3$, (14g, 0.105mole) were mixed, stirred and treated with a solution of 2-hydroxy-3-methylbenzoic acid chloride (12g, 0.07mole) in chlorobenzene (20ml). The mixture was stirred and heated at 100°C overnight. The cooled mixture was added to conc. HCl (10ml) and ice, extraction with ether, and ether washed with saturated sodium bicarbonate solution, dried ($Na_2SO_4$), filtered and the filtrate distilled, to give (after removal of the ether), a main fraction 2-hydroxy-3-methyl-4'-chlorobenzophenone, b.p. 148°–152°C/0.5mm (8.18g), which solidified to yellow microplates, m.p. 55°–58°C.

Found: C.68.23; H.4.71; Cl.14.61. $C_{14}H_{11}ClO_2$. Requires : C.68.16; H.4.49; Cl.14.37%.

EXAMPLE 31

2-Hydroxy-3-methyl-4'-chlorobenzophenone oxime

The ketone of Example 30 (7.5g,0.03mole) in ethanol (18ml) was added with stirring to a solution of (85%) potassium hydroxide (20.74g, 0.3mole) in water (85ml) at 10°C, this colloidal solution was treated with solid hydroxylamine hydrochloride (8.54g,0.12 mole) and stirred overnight. The solution was acidified with 5NHCl to give a solid, which was filtered, washed with water and stirred for 45 minutes, with 5% $Na_2CO_3$ solution (30.5ml), to remove unwanted oxime stereoisomer, filtered, washed with 5% $Na_2CO_3$ solution (100ml) and then with water until free of alkali. The dried solid had m.p. 175°–177°C. Recrystallisation from 54% benzene-light petroleum (b.p. 60°–80°C) mixture gave the oxime, m.p. 178°C ("bonded isomer") 5.45g.

Found : C.64.25; H.4.79; Cl. 13.41; N.5.3%; $C_{14}H_{12}Cl\ CO_2$. Requires: C.64.25; H.4.6; Cl. 13.55; N.5.35%.

EXAMPLE 32

2-Hydroxy-3-methyl-4'-chlorobenzophenone oxime acetate

Acetic anhydride (12ml) was warmed to 60°C and treated with the oxime of Example 31 (5.25g. 0.02mole). The stirred mixture was warmed to 80°C. to dissolve the oxime and the solution was then immediately cooled in an ice bath. The precipitated solid was filtered off, washed with light petroleum (b.p. 40°–60°) to give the acetate, 4.8g, m.p. 154°–156°C Found : C.63.18; H.4.86; Cl.11.5; N.4.77. $C_{16}H_{14}ClNO_3$. Requires C.63.26; H.4.64; Cl.11.67; N.4.6%.

EXAMPLE 33

3-p-Chlorophenyl-7-methyl-1,2-benzisoxazole

The oxime acetate of Example 32 (4.36g,0.014mole) was refluxed with sodium carbonate (3.3g; 0.031 mole) in triethylene glycol dimethyl ether (44ml) for 35 minutes. The mixture was poured into water (200ml), cooled in ice filtered and washed neutral with water. After drying the benzisoxazole (3.4g) had m.p. 88°–90°C and m.p. 97°–99° on recrystallisation from EtoH.

Found: C.68.87; H.4.37; Cl.14.82; N.5.83. $C_{14}H_{10}ClNO$. Requires :C.68.99; H.4.14; Cl.14.55; N.5.75.

EXAMPLE 34

3-p-Chlorophenyl-7-bromomethyl-1,2-benzisoxazole

The above benzisoxazole of Example 33 (28.9g, 0.1mole) with N-bromosuccimide (19.59g, 0.11mole) was refluxed in carbon tetrachloride (309ml) under illumination from an ultra-violet lamp (Hanovia type MPC) with stirring for three hours. The mixture was cooled and the solid succinimide was filtered off and washed with $CCl_4$. The filtrate was evaporated to dryness and the product recrystallised from light petroleum (b.p. 60°–80°)-$CCl_4$ to give the bromo-methyl compound (26.59g) m.p. 117°–120°C. ( containing a little 7-methyl starting material ).

Found : Br. 25.68; Cl. 10.75; N. 4.24; $C_{14}H_9BrClNO$. Requires: Br. 24.77; Cl. 10.99; N. 4.34%.

EXAMPLE 35

3-p-Chlorophenyl-1,2-benzisoxazol-7-yl-acetic acid

The bromomethyl compound of Example 34 (20g, 0.062mole) was stirred at room temperature in dimethyl formamide (190ml.) with sodium cyanide (3.03g, 0.062 mole) and sodium iodide (0.93g, 0.0062 mole) for 22 hours. The solution was evaporated to dryness to yield a solid which was treated with water, ground up, filtered and washed with water until the filtrate was free of halide ions. The dried crude nitrile (21.45g) had m.p. 110°–125°C, NMR showed that it contained 50% of the required product. The crude nitrile (20.67g, Ca 0.04 mole) was refluxed for four hours in conc.HCl.(207ml) and acetic acid (103 ml.). The mixture was poured into water (21.) to give a solid which was extracted with sodium carbonate solution, this was extracted with ether and the sodium carbonate solution was acidified to give the acetic acid which was recrystallised from 50% ethanol to give the acetic acid (2.76g), m.p. 198°–200°C.

Found : C. 62.84; H. 3.56; Cl. 12.55; N. 5.07; $C_{15}H_{10}ClNO_3$. Requires: C. 62.62; H. 3.5; Cl. 12.32; N. 4.87%.

EXAMPLE 36

α-Methyl-3-p-chlorophenyl-1,2-benzisoxazol-7-yl-acetic acid n-Butyl lithium (31ml, 46m Mole of 1.5M) was cooled to −30°C under nitrogen with stirring and treated with a solution of diisopropylamine (6.25 ml. 4.65g., 46m Mole) in tetrahydrofuran (38ml) keeping the temperature at −30° to −50°C. A solution of the acetic acid of Example 35 (4.5g, 15.64m Mole) in THF (38ml) and hexamethylphosphoramide (38ml) was added dropwise to the Bu Li solution and the solution stirred at −30° to −40°C for 1.5 hours. It was then transferred to a solution of methyliodide (150ml) which was stirred and had been cooled to 5° C. in an ice bath. The mixture was stirred in the melting ice bath for 1.5 hours, acidified with a little conc. HCl, evaporated to small bulk and treated with water (500ml). The mixture was extracted with chloroform which was dried ($Na_2SO_4$) and evaporated to leave the α-methyl acetic acid as a mixture with its methyl ester. This was refluxed with conc. HCl (60ml) and acetic acid (30ml) for four hours, diluted with water, extracted with chloroform, which was dried ($Na_2SO_4$), evaporated to leave a gum which was purified on preparative thin layer chromatography to give the α-methyl acetic acid (0.85g), m.p. 136°–138°C.

Found : C.63.88; H.4.27; Cl.11.46; N.4.65; $C_{16}H_{12}ClNO_3$. Requires: C. 63.69; H. 4.01; Cl. 11.75; N.4.64%.

EXAMPLE 37

2-Hydroxy-3-ethylbenzophenone

This compound (44.67g) was prepared from benzene (172g.,2.2 mole) and 2-hydroxy-3-ethyl benzoic acid chloride (63.15g,0.34 mole), using the same conditions as in Example 30. The b.p. of the compound was 123°–126°C./0.14mm, $\eta_D^{22}$ 1.6081,$\nu$max.(film) 1630cm$^{-1}$.

EXAMPLE 38 2-Hydroxy-3-ethylbenzophenone oxime

Using the conditions of Example 31, the ketone of Example 37 (45.34g,0.02mole) and hydroxylamine hydrochloride (56g,0.8 mole) gave the oxime (43.82g), m.p. 146°–148°C, $\nu$ max. (Nujol),3340,1650,1608,1600 cm$^{-1}$.

EXAMPLE 39

2-Hydroxy-3-ethylbenzophenone oxime acetate

The oxime of Example 38 (39.76g, 0.185 mole) (using the conditions of Example 32 above, followed by evaporation of the acetic anhydride and washing the product with light petroleum (b.p. 40°–60°) ), gave the acetate (40.45g), m.p. 63°–65°C, $\nu$ max. (Nujol) 1770 cm$^{-1}$.

EXAMPLE 40

3-Phenyl-7-ethyl-1,2-benzisoxazole

Using the conditions of Example 33, the acetate of Example 39 (39.34g, 0.145 mole) with sodium carbonate (31.86g, 0.3mole) in triethyleneglycol dimethyl ether (425ml) gave 3-phenyl-7-ethyl-1,2-benzisoxazole (27.32g) b.p. 129°–130°C/0.3mm, $\eta_D^{20}$ 1.6045, $\nu$ max. (film) 1625, 1608. NMR δ 1.42(3H) δ3.05 (2H), δ7.0–7.3 (8H)

EXAMPLE 41

3-Phenyl-7-α-bromoethyl-1,2-benzisoxazole

The 7-ethyl compound of Example 40 (2.23g, 10m Mole) in carbon tetrachloride (30ml) with N-bromosuccinimide (1.96g,11m Mole) and a trace of benzoyl peroxide or α-azo-isobutyronitrile was stirred and refluxed while being illuminated with ultra violet light for 2 hours. The cooled solution was filtered and the carbon tetrachloride evaporated off to leave the α-bromoethyl compound (3.18g) as an oil, $\eta_D^{23}$ 1.6280. $\nu$ max (film) 780, 1190cm$^{-1}$, NMR δ 1.22 (3H),δ 5.62 (1H), δ 7.0–8.0 (8H).

EXAMPLE 42

3-Phenyl-1,2-benzisoxazole-7-yl acetic acid

The α-bromoethyl compound of Example 41, (18.6g,16.55 m Mole) in dimethyl formamide (190ml) with sodium cyanide (3.02g.,61.55 m Mole) and sodium iodide (0.92g,15m Mole) was stirred at room temperature for 22 hours. The solution was evaporated to small bulk, the residue treated with water (200ml), extracted with chloroform (4×200ml), the $CHCl_3$ was washed with saturated sodium chloride solution and dried ($Na_2SO_4$), filtered and evaporated to give the crude α-cyanoethyl nitrile (25g) $\eta_D^{21}$ 1.5838, ν max. (film) 750cm$^{-1}$. The crude nitrile (25g) was stirred and refluxed in acetic acid (125ml) and conc. HCl for 4 hours. The mixture was poured into water (2500ml), extracted with $CHCl_3$, which was then extracted with sodium bicarbonate solution. The latter was acidified to yield an oil which was extracted with chloroform, dried ($Na_2SO_4$), filtered and evaporated to leave 3-phenyl-1,2-benzisoxazol-7-yl acetic acid (5.94g) as an oil, $\eta_D^{21}$ 1.5830. ν max (film) 2620, 1710, 750, 700 cm$^{-1}$, NMR δ 1.71 (3H), 4.42 (1H), 7.12–8.25 (8H), 9.95 (1H). Mass spectrum Parent ion m/e 267, others at 223 (loss of $CO_2$), 222 (loss of $CO_2H$), 208 (loss of $CH_3CO_2$), 195 (loss of $CH_3C.CO_2H$).

EXAMPLE 43

5-Ethyl-2-(4-chlorophenyl) benzoxazole

To a solution of hydrazine (0.7g) and water (0.36ml) was added a solution of 4'-chloro-5-ethyl-2-hydroxybenzophenone (2.6g) in ethanol (4ml.) The solution was refluxed for 1.5 hours then evaporated to dryness to give the crude hydrazone as a oil. $\eta^{22.5}$ 1.6245. A portion of this oil (0.27g) was added to a solution of 90% sulphuric acid (1.25ml) and sodium nitrite (0.1g) with cooling and stirring at a temperature below 15°C. There was effervescence and stirring was continued below 15°C until this subsided (~30mins). The mixture was added to ice/ammonium hydroxide and extracted with chloroform. T.L.C. showed that 5-ethyl-α-(4-chlorophenyl) benzoxazole had been produced.

EXAMPLE 44 a. 2-(p-Chlorophenyl)-5-ethyl benzoxazole

Polyphosphoric acid (wt. per ml. 2.1g) (495g), was warmed to 85°C on the steam bath and 4'-chloro-5-ethyl-2-hydroxybenzophenone oxime (25g, 0.09 mole) added in portions with stirring (temperature rose to 102°C). The reaction was stirred on a steam bath for 30 minutes. The mixture was poured into water (500ml) and stirred and cooled for 30 minutes. The solid was filtered (and some larger lumps of solid broken up) and washed with water (200ml). The solid was dried to give 24g. of crude product. This was recrystallised, with carbon treatment, from ethanol (250ml) to give a white solid (17.14g, 74%) m.p. 111°C, which was the title compound. GLC purity 99%. Material checked by NMR, GLC and T.L.C. Similarly prepared and characterised by NMR and T.L.C. were
 b. 2-(p-fluorophenyl)-5-ethyl benzoxazole;
 c. 2-(2,4-dichlorophenyl)-5-ethyl benzoxazole; and
 d. 2-(p-chlorophenyl)-6-ethyl benzoxazole

EXAMPLE 45 a. 2-p-Chlorophenyl-5-α-bromoethyl benzoxazole

The oxazole of Example 44(a) (200g, 0.776 mole) was stirred in carbon tetrachloride (2400ml), N-bromosuccinimide (152g, 0.854 mole) was added and the stirred mixture brought to the boil. The U.V. lamp (Hanovia type MPC, 125 watts, mounted outside the pyrex reaction vessel) was switched on. The progress of the reaction was monitored by gas chromatography and by this criterion was complete in six hours. The solution was allowed to cool overnight and then filtered to remove succinimide and the filtrate evaporated almost to dryness and then stirred with n-hexane (0.5-1 liter), filtered washed with hexane (¼ to ½ liter) and dried at 40°C/high vacuum to give the α-bromo compound (240.2 g, 92%) m.p. 110°-112°C (softening slightly at 107°C) NMR was in accordance with the expected structure. Similarly prepared and characterised by NMR were :
 b. 2-(p-fluorophenyl)-5-α-bromoethyl benzoxazole;
 c. 2-(2,4-dichlorophenyl)5-α-bromoethyl benzoxazole: and
 d. 2-(p-chlorophenyl)-6-α-bromoethyl benzoxazole.

EXAMPLE 46 a. 2-(2-p-chlorophenyl-5-benzoxazolyl)propionitrile

The α-bromo compound of Example 45(a) (166.4g, 0.49 mole) was stirred in dimethyl formamide (1584 ml, containing 0.32% $H_2O$ dried by distillation over anhydrous $K_2CO_3$) until it dissolved, then treated with powdered fused sodium iodide (7.4g, 0.049 mole) and partially powdered sodium cyanide (24.22g, 0.49 mole) with cooling to maintain the temperature at 15°-20°C. The solution was left overnight and then evaporated almost to dryness, treated with water, filtered, washed with water (approximately 5-7 liters) until the washings gave only a faint turbidity with $AgNO_3$ solution. Drying at 50°C/high vacuum was then carried out to give the title compound in high yield (m.p. 142°C). Similarly prepared were :
 b. 2-(2-p-fluorophenyl-5-benzoxazolyl)propionitrile;
 c. 2-[2-(2,4-dichlorophenyl)-5-benzoxazolyl]propionitrile; and
 d. 2-(2-p-chlorophenyl-6-benzoxazolyl)propionitrile

EXAMPLE 47 a. 2-(2-p-Chlorophenyl-5-benzoxazolyl) propionic acid

The nitrile of Example 46(a) (139.1g, 0.49 mole) was stirred and heated to 80°± 5°C in concentrated hydrochloric acid (1390 ml). The mixture (which became a solution) was stirred and heated at this temperature for two hours. It was then poured into water (approximately 7 liters) and the mixture cooled in ice to approximately 10°C. The initial precipitate which formed was filtered and washed with water, then dried to constant weight at 45°C/high vacuum. The product was the title compound in crude form (m.p. 165°-171°C). After recrystallisation from butyl acetate there was obtained pure 2-(2-p-chlorophenyl-5-benzoxazolyl)propionic acid (m.p. 190°C). Similarly prepared from the nitriles of Examples 46(b) and (c) were :
 b. 2-(2-p-fluorophenyl-5-benzoxazolyl) propionic acid (m.p. 163°C);
 c. 2-[2-(2,4-dichlorophenyl)-5-benzoxazolyl] propionic acid (m.p. 152°C); and,
 d. 2-(2-p-chlorophenyl-6-benzoxazolyl)propionic acid (m.p. 196°C)

In the following Examples of pharmaceutical compositions of the present invention, the term "medicament" is used to indicate the compound α-methyl-3-p-chlorophenyl-1,2-benzisoxazol-7-yl acetic acid. That compound may, of course, be replaced by any other active compound of formula I and the amount of medicament may be increased or decreased depending on the degree of activity of the medicament used.

EXAMPLE 48

Tablets each containing 100mg of medicament are made as follows:

| Medicament | 100mg |
|---|---|
| Potato starch | 38mg |
| Lactose | 25mg |
| Ethyl cellulose (as 20% solution in industrial alcohol) | 2mg |
| Alginic acid | 7mg |
| Magnesium stearate | 1mg |
| Talc | 2mg |
| Total | 175mg |

The medicament, starch and lactose are passed through a No. 44 mesh B.S.S. sieve and mixed thoroughly. The solution of ethyl cellulose is mixed with the resultant powders which are then passed through a No. 12 mesh B.S.S. sieve. The granules produced are dried at 50°–60°C. and then passed through No. 16 mesh B.S.S. sieve. The alginic acid, magnesium stearate and talc, previously passed through a No. 60 mesh B.S.S. sieve, are added to the granules, mixed and compressed in a tabletting machine to yield tablets each weighing 175 mg.

EXAMPLE 49

Capsules each containing 200 mg of medicament are made as follows:

| Medicament | 200 mg |
|---|---|
| Lactose | 48 mg |
| Magnesium stearate | 2 mg |

The medicament, lactose and magnesium stearate are passed through a No. 44 mesh B.S.S. sieve and filled into hard gelatine capsules in 250 mg quantities.

EXAMPLE 50

Injection solutions each containing 100 mg of medicament per 5 ml solution are made as follows:

| Medicament | 100 mg |
|---|---|
| Sodium hydroxide (10% solution) | q.s. |
| Water for injection | to 5 ml |

The medicament is suspended in the water and the sodium hydroxide solution added drop by drop with stirring until the medicament is in solution. The pH of the solution is adjusted to between 8.0 and 8.5, the solution is sterilised by filtration through a bacteria-proof filter and filled into previously sterilised glass ampoules which are then hermetically sealed under aseptic conditions.

EXAMPLE 51

Suppositories each containing 250 mg of medicament are made as follows:

| Medicament | 250 mg |
|---|---|
| Theobroma Oil | to 2000 mg |

The medicament is passed through a No. 60 mesh B.S.S. sieve and suspended in the theobroma oil previously melted using the minimum of heat necessary. The mixture is then poured into a suppository mould of nominal 2 g capacity and allowed to cool.

We claim:

1. A 1,2-benzisoxazole derivative of formula I:

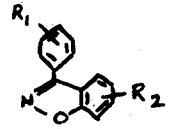

wherein $R^1$ represents one or two substituents substituted in any of the available positions in the benzene ring selected from the class consisting of hydrogen, chlorine, bromine, $C_{1-4}$ alkyl, $C_1-C_4$ alkoxy, nitro, and trifluoromethyl, and $R^2$ is a substituent at the 5-, 6-, or 7- position of the 1,2-benzisoxazole nucleus and is one of the following: carboxy $C_{1-4}$ alkyl, —CH($R^3$).COOH, —CH$_2$.COOR$^3$ and —CH($R^3$).COOR$^3$, where $R^3$ is $C_{1-4}$ alkyl; and pharmaceutically acceptable salts thereof when $R^2$ is carboxy $C_{1-4}$ alkyl or CH($R^3$).COOH.

2. A 1,2-benzisoxazole as claimed in claim 1 wherein $R^2$ is —CH$_2$COOH or —CH(Me)COOH.

3. A 1,2-benzisoxazole as claimed in claim 2, wherein $R^1$ is a parahalo substituent.

4. α-Methyl-3--p-chlorophenyl-1,2-benzisoxazol-7-yl acetic acid.

* * * * *

UNITED STATES PATENT AND TRADEMARK OFFICE
CERTIFICATE OF CORRECTION

PATENT NO. : 3,951,999
DATED : April 20, 1976
INVENTOR(S) : John Christopher Saunders, et al.

It is certified that error appears in the above-identified patent and that said Letters Patent are hereby corrected as shown below:

Column 9, line 50, "benzioxazol-5-]" should read --benzisoxazol-5-yl]--

Column 12, line 23, "$C_{15}H_{14}ClNO$ " should read --$C_{15}H_{14}ClNO_2$--

Column 16, line 44, "870" should read --87.0--.

Signed and Sealed this twelfth Day of July 1977

[SEAL]

Attest:

RUTH C. MASON
*Attesting Officer*

C. MARSHALL DANN
*Commissioner of Patents and Trademarks*